(12) United States Patent
Vardi

(10) Patent No.: US 7,914,578 B2
(45) Date of Patent: Mar. 29, 2011

(54) METHOD AND APPARATUS FOR EXPANDING TISSUE

(76) Inventor: Gil Vardi, Town and Country, MO (US)

( * ) Notice: Subject to any disclaimer, the term of this patent is extended or adjusted under 35 U.S.C. 154(b) by 999 days.

(21) Appl. No.: 11/256,906

(22) Filed: Oct. 24, 2005

(65) Prior Publication Data

US 2007/0093866 A1  Apr. 26, 2007

(51) Int. Cl.
*A61F 2/12* (2006.01)
*A61M 29/00* (2006.01)

(52) U.S. Cl. .......................................... 623/8; 606/198

(58) Field of Classification Search ............... 623/7–8, 623/23.64–23.67, 23.69–23.71; 604/93.01, 604/95.04, 96.01; 128/898–899
See application file for complete search history.

(56) References Cited

U.S. PATENT DOCUMENTS

| | | |
|---|---|---|
| 4,157,085 A | 6/1979 | Austad |
| 4,950,258 A * | 8/1990 | Kawai et al. ............ 604/530 |
| 4,950,292 A * | 8/1990 | Audretsch ............... 623/8 |
| 5,033,481 A * | 7/1991 | Heyler, III ............... 623/8 |
| 5,074,878 A | 12/1991 | Bark et al. |
| 5,425,762 A | 6/1995 | Muller |
| 5,496,368 A | 3/1996 | Wiese |
| 5,618,310 A * | 4/1997 | Ger et al. ................ 606/216 |
| 5,632,774 A | 5/1997 | Babian |
| 5,713,960 A | 2/1998 | Christensen et al. |
| 6,203,570 B1 | 3/2001 | Backe |
| 6,231,605 B1 | 5/2001 | Ku |
| 6,254,624 B1 * | 7/2001 | Oddsen et al. ........... 606/213 |
| 6,371,984 B1 | 4/2002 | Van Dyke et al. |
| 6,699,176 B1 | 3/2004 | Khouri |
| 6,752,814 B2 * | 6/2004 | Gellman et al. .......... 606/148 |
| 6,764,514 B1 | 7/2004 | Li et al. |
| 6,783,546 B2 | 8/2004 | Zucherman et al. |
| 7,166,127 B2 * | 1/2007 | Spence et al. ............ 623/2.37 |
| 7,445,630 B2 * | 11/2008 | Lashinski et al. ........ 623/2.1 |
| 2001/0032019 A1 | 10/2001 | Van Dyke et al. |
| 2004/0211434 A1 * | 10/2004 | Loomas et al. .......... 128/898 |
| 2004/0215339 A1 * | 10/2004 | Drasler et al. ........... 623/3.1 |
| 2005/0004681 A1 * | 1/2005 | Stack et al. .............. 623/23.65 |
| 2005/0149159 A1 | 7/2005 | Andreas et al. |
| 2006/0136056 A1 * | 6/2006 | Wohl ........................ 623/8 |

FOREIGN PATENT DOCUMENTS

WO  2007051104 A2  5/2007

OTHER PUBLICATIONS

Ryhanen et al, "In vivo biocompatibility evaluation of nickel-titanium shape memory metal alloy: Muscle and perineural tissue responses and encapsule membrane thickness," Jan. 19, 1998, Journal of Biomedical Materials Research, 41, 481.*

International Search Report, International App. No. PCT/US06/60189 (Sep. 12, 2007).

* cited by examiner

*Primary Examiner* — Suzette J Gherbi
(74) *Attorney, Agent, or Firm* — Armstrong Teasdale LLP

(57) ABSTRACT

An implantable tissue expander for supporting a body tissue including a support member positioned with respect to the body tissue and adapted to expand to a support configuration, in the support configuration, the support member shaping the body tissue.

1 Claim, 5 Drawing Sheets

METHOD AND APPARATUS FOR EXPANDING TISSUE

BACKGROUND OF THE INVENTION

This invention relates generally to tissue expansion, and more particularly, to methods and apparatus for supporting, sculpting and/or shaping tissue.

Tissue expanders, such as implants, bladders, envelopes and the like, are typically placed within the body to expand, reconstruct, or otherwise augment missing or misshapen body tissue. For example, a tissue expander may be used to augment, sculpt, and support soft tissue, such as breast, penile, gluteal, and facial tissue.

Soft tissue augmentation and reconstruction, for example breast augmentation and reconstruction, is known and has been performed by physicians for decades. The use of silicone gel-filled implants may provide improved appearance, but silicone gel-filled envelopes create safety concerns for manufacturers, physicians, and patients due to possible leaks of the silicone gel into the body. Saline-filled implants have been used in place of silicone gel-filled implants, but have a less natural shape and consistency.

Another aspect in the field of breast augmentation and reconstruction is the use of tissue expanders. Tissue expanders typically include a bladder or envelope that holds a liquid, such as saline or a hydro-gel. The tissue expander is implanted under tissue, such as under the muscle below a surgically removed breast. A small amount of liquid is added to the envelope periodically until the desired size is reached. By adding liquid slowly over a period of weeks or months, the covering tissue is allowed to expand to accommodate its size. However, in order to change the volume of the tissue expander a needle must be inserted into the envelope each time.

BRIEF DESCRIPTION OF THE INVENTION

In one aspect, an implantable tissue expander for supporting a body tissue is provided. The implantable tissue expander includes a support member positioned with respect to the body tissue. The support member has shape memory properties and is adapted to expand to a support configuration. In the support configuration, the support member shapes the body tissue.

In another aspect, an implantable tissue expander for supporting a body tissue is provided. The implantable tissue expander includes a support member adapted to be positioned with respect to the body tissue in a support configuration. A first end of the support member is positioned with respect to a first portion of the body tissue and an opposing second end of the support member is positioned with respect to a second portion of the body tissue. The first end and the second end each transitions into a body of the support member, which includes a biasing element. In the support configuration, the biasing element exerts a force at each of the first end and the second end to support the body tissue.

In another aspect, a method for supporting a body tissue is provided. The method includes positioning at least one tissue expander with respect to the body tissue and expanding the at least one tissue expander to a support configuration to support and shape the body tissue.

DETAILED DESCRIPTION OF THE INVENTION

Figure 1:
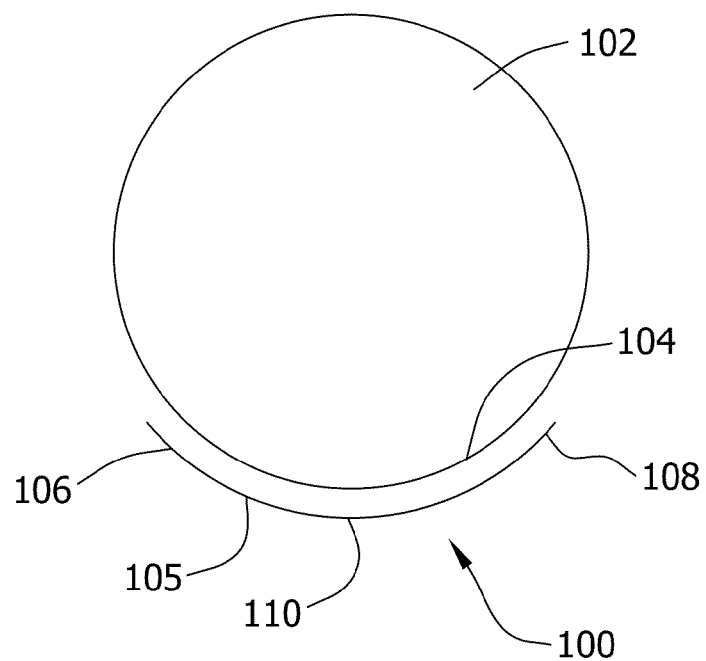
FIG. 1 is a front view of a tissue expander positioned with respect to a breast, according to one embodiment of this invention.

FIG. 1 is a front view of an implantable tissue expander 100 for supporting, shaping and/or sculpting a body tissue. While the tissue expander is described in terms of certain specific embodiments, it is not intended to be limited to these embodiments. For example, components used within the tissue expander may have a variety of shapes, sizes, and/or uses. It will be apparent to one of ordinary skill in the art, however, that the tissue expander may be practiced without limitation to any specific detail presented herein. For example, tissue expander 100 can be used in conjunction with a plurality of delivery systems including, but not limited to, a catheter delivery system and a surgical implantation system.

Referring to FIG. 1, in an exemplary embodiment, a breast 102 is illustrated with tissue expander 100 positioned at a base portion 104 of breast 102. The invention is not limited to the expansion, reconstruction, and/or augmentation of a breast. For example, the invention may be used to expand, reconstruct, and/or augment penile, gluteal, and/or facial tissue. Furthermore, the invention may be used in a variety of soft body tissue areas where expansion, reconstruction, and/or reconstruction is practiced.

In the exemplary embodiment, tissue expander 100 includes a support member 105 having a first end 106, an opposing second end 108, and a body 110 extending therebetween, as shown in FIG. 1. Tissue expander 100 may have any suitable size and/or shape. In the exemplary embodiment, tissue expander 100 has a generally arcuate or semi-circular shape or configuration. In alternative embodiments, the shape and/or size of tissue expander 100 is selected to correspond to a shape, a size, and/or location of the body tissue within the patient's body. For example, in alternative embodiments, support member 105 is one of a rod, a wire, and a ribbon having flat surfaces and/or round surfaces, and having a hollow or solid cross-sectional area.

Tissue expander 100 is adapted to expand from an initial insertion configuration to a support configuration for supporting and/or shaping the body tissue. In the exemplary embodiment, tissue expander 100 has a circular cross-section and is radially expandable. In one embodiment, tissue expander 100 is radially expandable between a generally unexpanded or insertion diameter and an expanded or support diameter which is greater than the insertion diameter. As such, tissue expander 100 is flexible and can be coupled to a catheter in a radially compressed configuration, i.e. the insertion configuration, for introduction and positioning with respect to the body tissue. Upon positioning of tissue expander 100, tissue expander 100 is expandable to the support configuration. In one embodiment, tissue expander 100 is expandable using a spring-like action and/or memory properties of the material, for example. As such, tissue expander 100 is radially distensible and/or deformable. In one embodiment of this invention, tissue expander 100 includes support member 105 fabricated using a suitable material having shape memory properties that are effected by changes in temperature or that have super elastic properties. It will be understood that various other means for expanding or enabling the expansion of tissue expander 100 may be employed without departure from the scope of this invention.

In one embodiment, tissue expander 100 including support member 105 is fabricated from any suitable biocompatible material including, without limitation, suitable metal materials, such as stainless steel, platinum, gold, titanium, and alloys and/or composites thereof, as well as suitable polymeric materials. In the exemplary embodiment, tissue expander 100 is fabricated from Nitinol which has the ability to perform well while in a spring-like configuration, and/or in a shape memory configuration.

In an alternative embodiment, tissue expander 100 includes a plurality of magnets and/or magnetic components positioned with respect to tissue expander 100 to affect a final shape of tissue expander 100 in the support configuration. For example, a first magnet is positioned at first end 106 of support member 105 and a second magnet is positioned at opposing second end 108 to magnetically move first end 106 towards or away from second end 108 and, thus, support and/or shape the body tissue.

Figure 2:
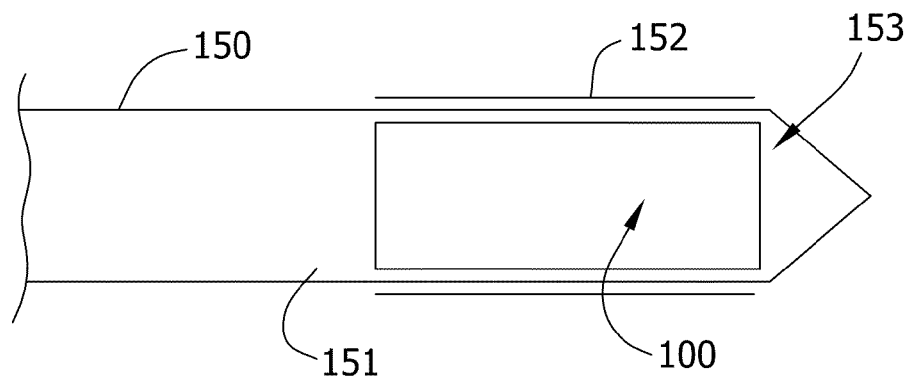
FIG. 2 is a partial cross-sectional view of the tissue expander shown in FIG. 1 positioned within a catheter delivery system, according to one embodiment of this invention.
Figure 3:
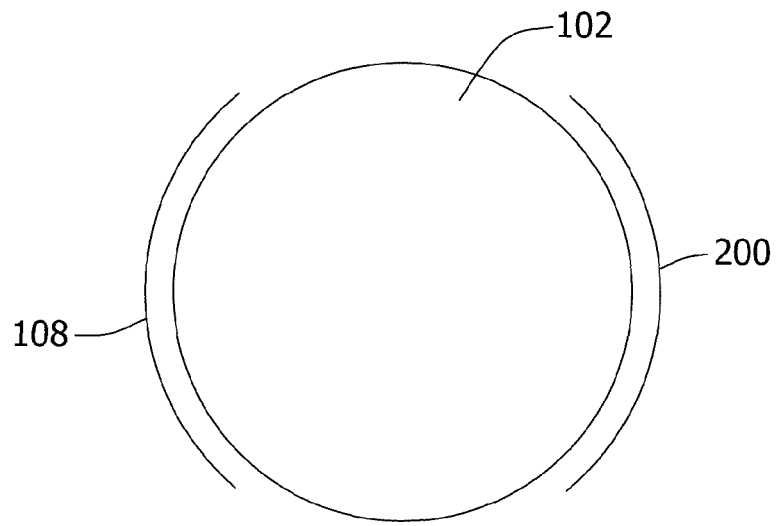
FIG. 3 is a front view of a first tissue expander and a second tissue expander positioned with respect to a breast, according to one embodiment of this invention.

FIG. 2 is a partial cross-sectional view of tissue expander 100 positioned within a catheter delivery system 150. In the exemplary embodiment, tissue expander 100 is configured to be delivered by catheter system 150. For example, tissue expander 100 is bendable or shapeable into an insertion configuration for positioning within catheter delivery system 150. Catheter delivery system 150 is inserted into the patient's body by percutaneous delivery. A guide wire is used to advance catheter delivery system 150, depending on the location of the soft body tissue within the patient's body. In one embodiment, tissue expander 100 and a tissue expander 200 are introduced using catheter delivery system 150 and at least a portion of tissue expander 100 and tissue expander 200 are aligned with each other, as shown in FIG. 3. In one embodiment, at least one radio-opaque marker is utilized to monitor the alignment of tissue expander 100 with tissue expander 200. Alternatively, tissue expander 100 is introduced using catheter delivery system 150 and tissue expander 200 is introduced using a second catheter delivery system, similar to catheter delivery system 150, without using radio-opaque markers.

As shown in FIG. 2, catheter delivery system 150 includes a catheter 151 forming a chamber 153. Tissue expander 100 is positionable within chamber 153 in an insertion configuration for introduction into the desired body tissue region or location. In the insertion configuration, tissue expander 100 is generally straight or linear. A catheter sheath 152 covers at least a portion of tissue expander 100 in the insertion configuration for introduction into the desired body tissue region or location. Catheter sheath 152 forms a housing, a sleeve, a sock or a suitable assembly for surrounding and retaining tissue expander 100 in the unexpanded or insertion configuration within catheter delivery system 150. As such, in the exemplary embodiment, sheath 152 is tubular in shape. In the exemplary embodiment, sheath 152 is sized to overlay at least tissue expander 100 and catheter 151. In alternative embodiments, sheath 152 may have any suitable shape and/or size. In one embodiment, sheath 152 is a retractable. In another embodiment, sheath 152 is configured to move in a distal direction and a proximal direction with respect to or along catheter 151 to aid in the deployment of tissue expander 100. In one aspect, sheath 152 has a yield strength greater than an expansion force of tissue expander 100. As such, sheath 152 retains tissue expander 100 in the unexpanded or insertion configuration during delivery and introduction of tissue expander 100.

During positioning of tissue expander 100 with respect to breast 102, sheath 152 retracts to proximally release tissue expander 100. In one embodiment, tissue expander 100 begins to expand as it exits sheath 152. In another embodiment, tissue expander 100 expands at a selected temperature. In yet another embodiment, a balloon is inflatable to expand tissue expander 100. After deployment of tissue expander 100, catheter 151, including sheath 152, is withdrawn from the body tissue location, leaving tissue expander 100 properly positioned with respect to the body tissue.

Exemplary embodiments of tissue expanders are described below. The embodiments described herein are illustrated with reference to the figures wherein similar numbers indicate the same elements in all figures. Such figures are intended to be illustrative rather than limiting and are included herewith to facilitate explanation of an exemplary embodiment of the tissue expander.

FIG. 3 is a front view of tissue expander 100 and a second tissue expander 200. Tissue expander 200 is similar to tissue expander 100 except as specifically set forth below. Tissue expander 100 and tissue expander 200 are positioned generally vertically with respect to opposing side portions of breast 102 and provide support to breast 102 superiorly to inferiorly.

Figure 4:
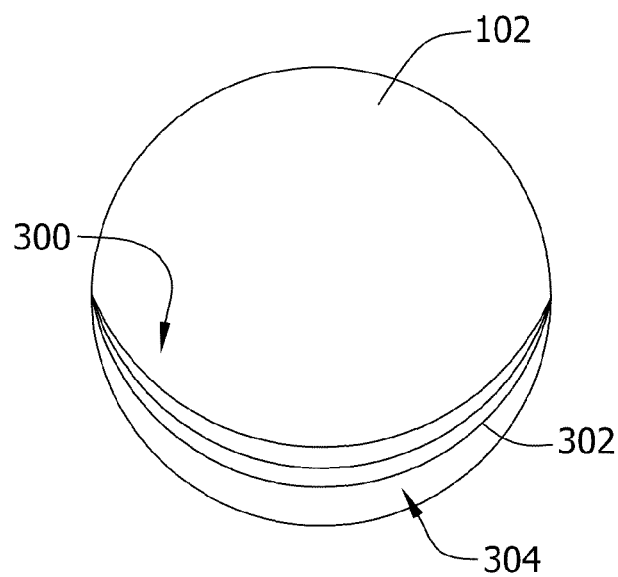
FIG. 4 is a front view of a tissue expander including a plurality of support members positioned with respect to a breast, according to one embodiment of this invention.

FIG. 4 is a front view of a tissue expander 300. In the exemplary embodiment, tissue expander 300 includes a plurality of support members 302. In this embodiment, each support member 302 is similar to support member 105, discussed above, and connected to adjacent support members 302 at opposing end portions of tissue expander 300. Each support member 302 is expandable with respect to adjacent support members 302 to form tissue expander 300 for supporting and/or shaping the body tissue, as shown in FIG. 4. In one embodiment, tissue expander 300 has a shape that is one of arcuate and semi-circular with a curvilinear cross-section. In alternative embodiments, tissue expander 300 has a triangular shape. Tissue expander 300 is configured to be positioned in or with respect to a lower portion 304 of breast 102, as shown in FIG. 4, to support, shape and/or sculpt breast 102.

Tissue expander 300 is flexible and can be initially coupled to a catheter delivery system, such as catheter delivery system 150, in a compressed insertion configuration and expanded within the body tissue location to a support configuration. Each support member 302 of tissue expander 300 is expandable using a spring-like action and/or shape memory properties of the material, for example. In one embodiment, support members 302 include a suitable material having shape memory properties reactive or responsive to temperature changes. As such, support members 302 are distensible and/or deformable.

Figure 5:
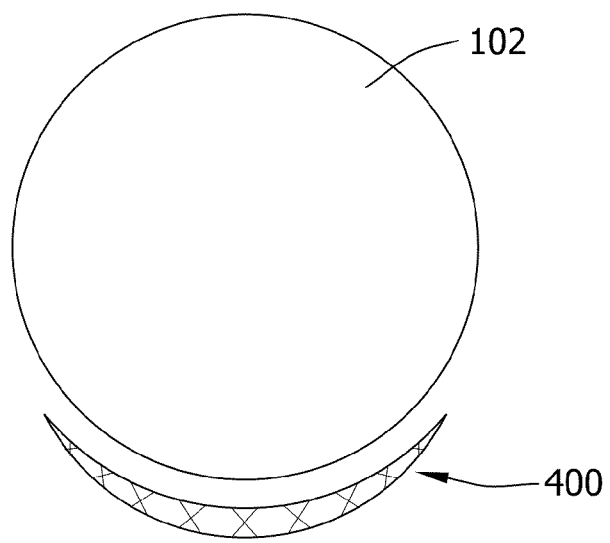
FIG. 5 is a front view of a tissue expander positioned with respect to a breast, according to one embodiment of this invention.

FIG. 5 is side view of a mesh tissue expander 400. In the exemplary embodiment, tissue expander 400 has a tubular mesh configuration and is radially expandable. In one embodiment, mesh tissue expander 400 is radially expandable between a generally unexpanded or insertion configuration having an insertion diameter and an expanded or support configuration having a support diameter which is greater than the insertion diameter. As such, mesh tissue expander 400 is flexible and can be initially coupled to a catheter in a radially compressed insertion configuration and expanded within the body tissue location to a support configuration. In one embodiment, tissue expander 400 is expandable using a spring-like action and/or shape memory properties of the material, for example. Tissue expander 400 includes a suitable material having shape memory properties reactive or responsive to temperature changes. In another embodiment, tissue expander 400 is expandable by balloon expansion or inflation. As such, tissue expander 400 is radially distensible and/or deformable. Other suitable means for expanding or enabling the expansion of tissue expander 400 may be employed without departure from the scope of this invention.

In one embodiment, tissue expander 400 is fabricated from Nitinol. Other suitable biocompatible materials, including metal materials, such as stainless steel, platinum, gold, titanium, alloys and/or composites, as well as polymeric materials can be used to fabricate tissue expander 400.

Figure 6:
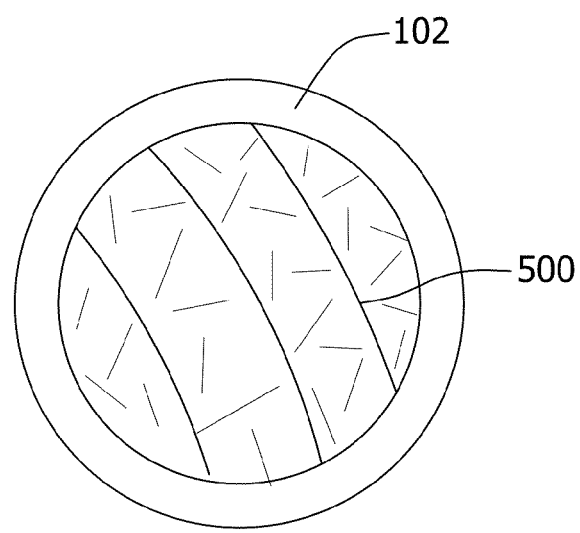
FIG. 6 is a front view of a tissue expander positioned with respect to a breast, according to one embodiment of this invention.

FIG. 6 is a front view of a tissue expander 500. In the exemplary embodiment, tissue expander 500 is fabricated using a suitable biocompatible material, such as materials discussed above in reference to tissue expanders 100 and 400. In the exemplary embodiment, tissue expander 500 has a generally spherical shape having a hollow interior. In alternative embodiments, tissue expander 500 has a generally solid interior. Tissue expander 500 is radially expandable between a generally unexpanded or insertion configuration having an unexpanded or insertion diameter and an expanded or support configuration having an expanded or support diameter which is greater than the insertion diameter. Tissue expander 500 is inserted into the patient's body using a suitable insertion instrument, such as catheter delivery system 150. After tissue expander 500 is positioned with respect to the body tissue, as desired, tissue expander 500 expands and increases in diameter from the insertion diameter to the desired or selected support diameter to support, sculpt, and/or shape the body tissue.

Figure 7:
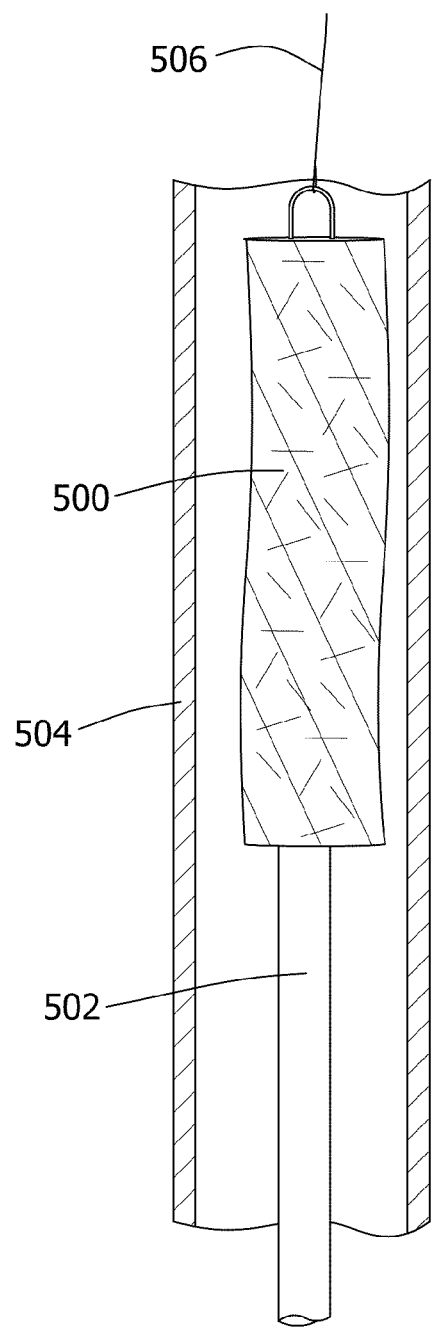
FIG. 7 shows the tissue expander of FIG. 6 positioned in a collapsed configuration within a catheter, according to one embodiment of this invention.

In one embodiment, tissue expander 500 is initially positioned in a collapsed position about or within a catheter 502, as shown in FIG. 7. A sheath 504 is positioned about tissue expander 500 and at least a portion of catheter 502. In the collapsed position, tissue expander 500 is positioned with respect to the body tissue, as desired. In one particular embodiment, a suitable guide wire 506 positions tissue expander 500. With tissue expander 500 positioned as desired, sheath 504 is movable along a length of catheter 502 to expose tissue expander 500. Tissue expander 500 expands, as shown in FIG. 6, to support, sculpt, and/or shape the body tissue. In one embodiment, a balloon is used to expand tissue expander 500. Tissue expander 500 increases in volume to expand to a generally spherical shape having a hollow interior. In alternative embodiments, tissue expander 500 has a generally solid interior in the expanded configuration. Further, in alternative embodiments, tissue expander 500 has any suitable expanded shape. In this embodiment, tissue expander 500 is fabricated using a Nitinol material skeleton including a covering cloth. In alternative embodiments, tissue expander 500 includes the skeleton without the covering cloth.

Figure 8:
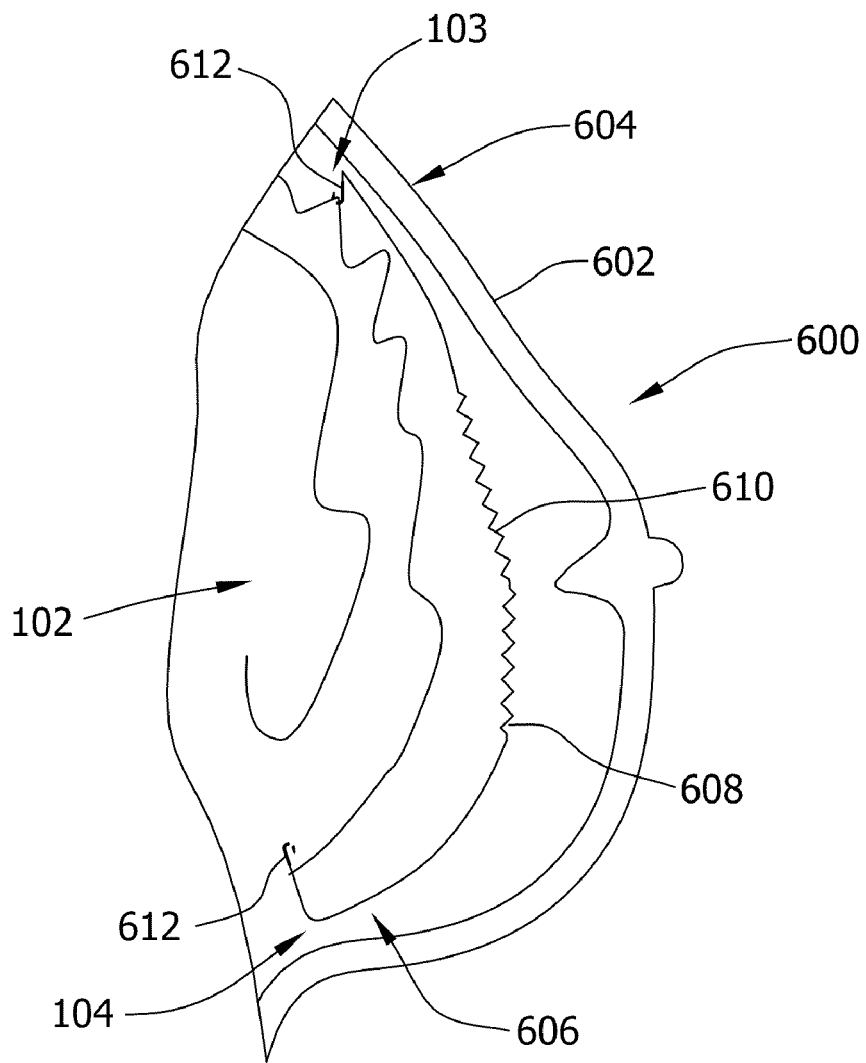
FIG. 8 is a side view of a tissue expander positioned with respect to a breast, according to one embodiment of this invention

In one embodiment, implantable tissue expander 600 is adaptable to be positioned with respect to a body tissue, for example a breast 102 as shown in FIG. 8, to support, sculpt, and/or shape the body tissue.

Tissue expander 600 is flexible and can be initially coupled to a catheter delivery system, such as catheter delivery system 150, in a compressed insertion configuration and expanded within the body tissue location to a support configuration. Tissue expander 600 is expandable using a spring-like action and/or shape memory properties of the material, for example. In one embodiment, tissue expander 600 includes a suitable material having shape memory properties reactive or responsive to temperature changes. As such, tissue expander 600 is distensible and/or deformable.

Tissue expander 600 includes a support member 602 adapted to be positioned with respect to breast 102 in a support configuration, as shown in FIG. 8. In one embodiment, first end 604 of support member 602 is positioned with respect to a first portion of breast 102, for example a superior region or location 103 of breast 102. An opposing second end 606 of support member 602 is positioned with respect to a second portion of the body tissue, for example an inferior or base region or location 104 of breast 102. It is apparent to those skilled in the art that support member 602 may be positioned in any desirable orientation or position with respect to breast 102. For example, support member 602 may be positioned in a generally vertical orientation or position with respect to breast 102, as shown in FIG. 8. In an alternative embodiment, support member 602 is positioned in a generally horizontal or lateral orientation or position with respect to breast 102. In a further embodiment, one or more support members 602 are used in one or more of a generally vertical, lateral and/or diagonal orientation or position to support, sculpt, and/or shape breast 102, as desired.

In one embodiment, first end 604 forms or includes a suitable fastener 612 such as at least one hook or needle, which is inserted into the body tissue to secure first end 604 to superior region 103 of breast 102. Similarly, a suitable fastener 612 connected to or formed by second end 606 is inserted into the body tissue to secure second end 606 to inferior region 104 of breast 102. It is apparent to those skilled in the art that fastener 612 may include any suitable fastener or connector that can be inserted into the body tissue and remain securely connected to the body tissue to maintain first end 604 and second end 606 properly positioned with respect to the body tissue.

First end 604 and second end 606 transition into a body 608 of support member 602. In one embodiment, body 608 includes a biasing element 610, such as a spring, a coil and/or at least one magnet, which provides a force suitable to support, sculpt, and/or shape the body tissue, as desired. In the support configuration, biasing element 610 exerts a tension force at first end 604 and/or second end 606 to support breast 102. In one embodiment, biasing element 610 is generally positioned at a mid-section of support member 602 to provide a generally equal amount of force to first end 604 and second end 606. In another embodiment, biasing element 610 is positioned on support member 602 at a suitable location to provide a desired or selected force to first end 604 and/or second end 606.

While the invention has been described in terms of various specific embodiments, those skilled in the art will recognize that the invention can be practiced with modification within the spirit and scope of the claims.

What is claimed is:

1. An implantable tissue expander for supporting a body tissue comprising:

a support member adapted to be implanted and positioned externally with respect to the body tissue to be supported in a support configuration, a first end of said support member comprising a first fastener configured to be inserted into a first portion of the body tissue to secure said first end to the first portion and an opposing second end of said support member comprising a second fastener configured to be inserted into a second portion of the body tissue to secure said second end to the second portion, each of said first end and said second end transitioning into a body of said support member, said body including a biasing element, in said support configuration, said biasing element exerting a force at each of said first end and said second end to support the body tissue, said biasing element comprising one of a spring, a coil and at least one magnet.

* * * * *